US00PP15977P2

(12) United States Plant Patent
Falstad

(10) Patent No.: US PP15,977 P2
(45) Date of Patent: Sep. 20, 2005

(54) ***HOSTA* PLANT NAMED 'DANCING IN THE RAIN'**

(50) Latin Name: *Hosta hybrida*
Varietal Denomination: Dancing in the Rain

(75) Inventor: Clarence H. Falstad, Holland, MI (US)

(73) Assignee: Walters Gardens Inc., Zeeland, MI (US)

( * ) Notice: Subject to any disclaimer, the term of this patent is extended or adjusted under 35 U.S.C. 154(b) by 98 days.

(21) Appl. No.: 10/849,719

(22) Filed: May 20, 2004

(51) Int. Cl.[7] ..... A01H 5/00
(52) U.S. Cl. ..... Plt./353
(58) Field of Search ..... Plt./353

*Primary Examiner*—Anne Marie Grunberg
*Assistant Examiner*—Annette H Para

(57) ABSTRACT

A new and distinct cultivar of *Hosta* plant named 'Dancing in the Rain', characterized by leaves having deep green margins and a creamy yellow to creamy white center, with lavender flowers held nicely above foliage.

2 Drawing Sheets

Botanical classification: *Hosta hybrida* (Tratt.).
Variety denomination: 'Dancing in the Rain'.

BACKGROUND OF THE INVENTION

The present invention relates to the new and distinct cultivar of *Hosta,* botanically known as *Hosta* hybrid (Tratt.), and hereinafter referred to as the cultivar 'Dancing in the Rain'.

The new plant was discovered in July 1999 by the inventor, Clarence H. Falstad, III, as a non-induced, naturally occurring somaclonal variation of *Hosta* 'Blue Umbrellas' (not patented) in the plant tissue culture laboratory at a nursery in Zeeland, Mich., USA. Asexual propagation of the plant at the same nursery by tissue culture and division has shown that the unique and distinct characteristics of this new plant are stable and reproduce true to type in successive generations.

SUMMARY OF THE INVENTION

*Hosta* 'Dancing in the Rain' is unique from its parent sport, *Hosta* 'Blue Umbrellas', and all other *Hosta* cultivars, in several traits. *Hosta* 'Blue Umbrellas' is a very large *Hosta* cultivar of unknown parentage having large dark green leaves with a slight glaucous surface. 'Dancing in the Rain' has a cream-colored viridescent center and dark green to blue-green margin. During summers with temperatures in excess of 35 degrees C., and on young potted plants grown under similar warm conditions, the color of the leaf center shifts from the initial creamy white to a white with green misting, and then to nearly solid light green. Temperatures between 30 and 35 C. cause the plant to develop only the green misting. This transition is only a seasonal phenotype change, and does not reflect any change in genotype. The following spring the plant emerges with the same cream-colored center to the leaves.

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED BOTANICAL DESCRIPTION

Figure 1:
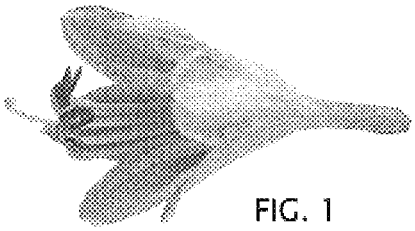
FIG. 1 shows the flower.
Figure 2:
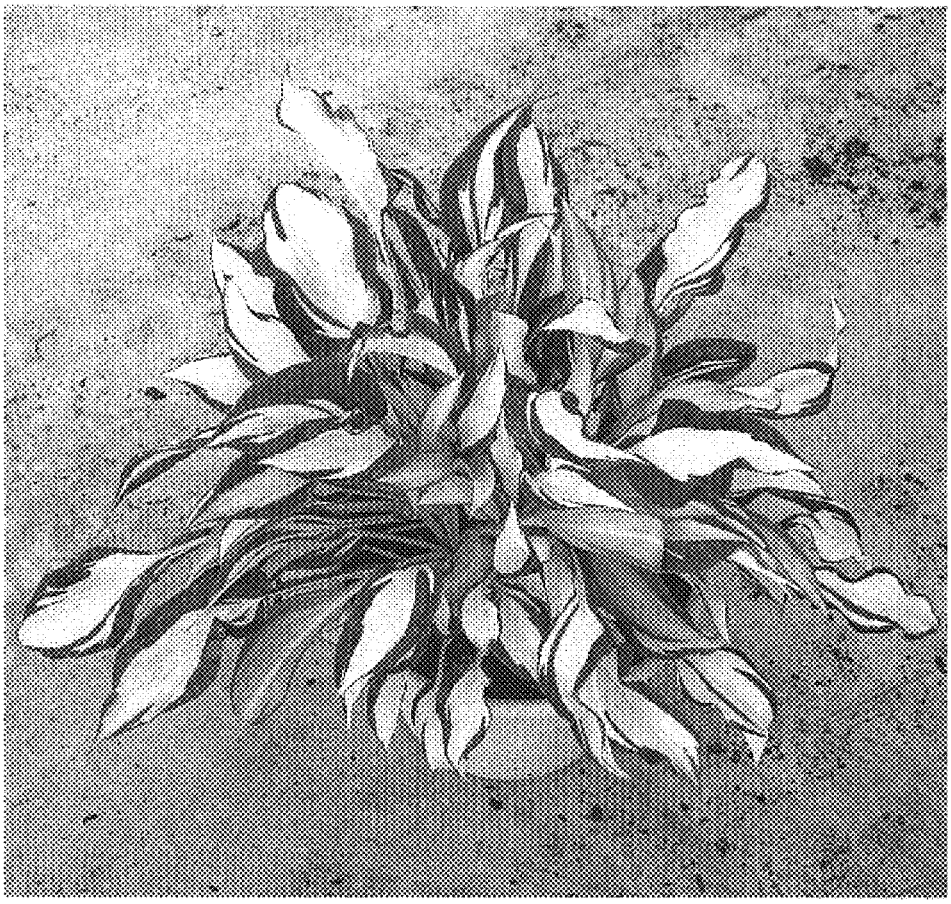
FIG. 2 shows the plant.
Figure 3:
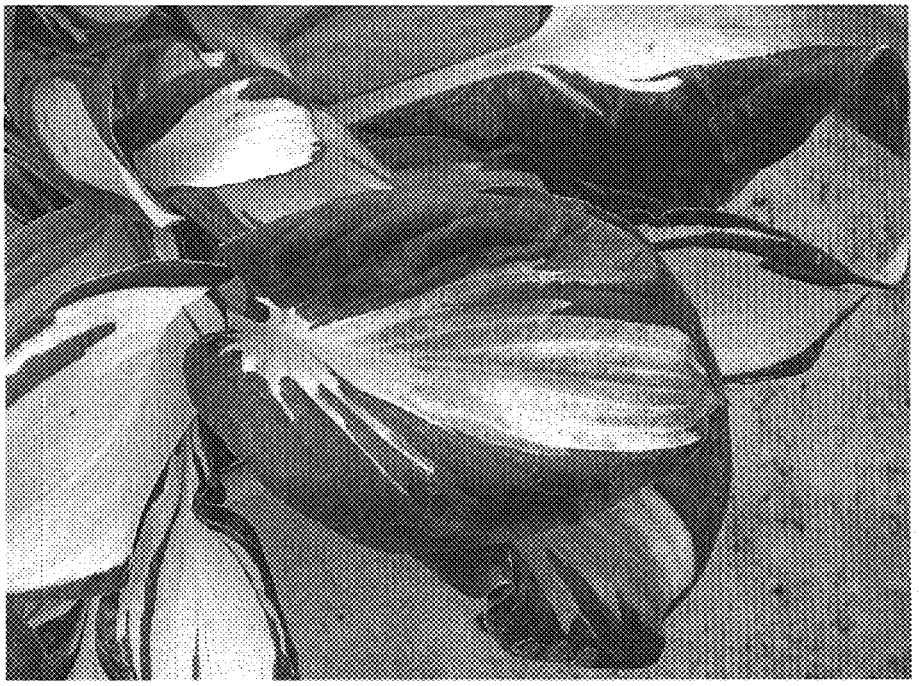
FIG. 3 shows a leaf with beginnings of the viridescent green blush.
Figure 4:
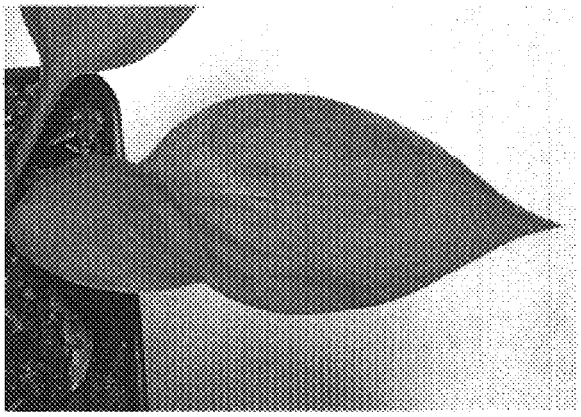
FIG. 4 shows the leaf of a young plant having gone nearly completely green.

The following descriptions and color references are based on The Royal Horticultural Society Colour Chart (2001 edition) except where common dictionary terms are used. The new plant, *Hosta* 'Dancing in the Rain', has not been observed under all possible environments. The phenotype may vary slightly with different environmental conditions, such as temperature, light, fertility and moisture, but without any change in the genotype. The following observations and size descriptions are of a three-year old plant in a one gallon container grown in Zeeland, Mich., USA under 50% shade on cloudless days, day temperatures of 18 to 28 degrees C., and night temperatures of 15 to 20 C.

Botanical classification: *Hosta* hybrid cultivar 'Dancing in the Rain'.

Parentage: Naturally occurring uninduced somaclonal variation of *Hosta* 'Blue Umbrellas' (not patented).

Propagation: Method by tissue culture and division. Time to initiate roots from both division and tissue culture three to four weeks from cutting.

Rooting habit: Normal, fleshy, to 3 mm thick, lightly branching.

Plant habit: Herbaceous, densely rhizomatous perennial, symmetrical with radical leaves upright and erect through flowering period, more horizontal late in the season and in maturity.

*Crop time.*—Under normal summer greenhouse growing conditions about 22 weeks to finish in a one-liter container; plant vigor is good especially for a *hosta* with white-centered leaves.

*Plant size.*—At flowering is 18 to 24 cm tall and 25 to 30 cm wide.

Foliage description:

*Shape and size.*—Ovate to broadly ovate leaf blades have a sharply acute apex when mature and cordate base. The leaf blades are 13 to 16 cm long and 8 to 10 cm wide.

*Color.*—Adaxial surface is a deep green closest to RHS 141 A on the margin of young emerging leaves. Later in the growing season, the margin is between RHS 139 A and RHS 136 A. As leaves are first emerging, the inside, or center portion of the leaf is yellow-green, more green than RHS 151 C. The center of the leaves then lightens to between yellow RHS 11 D to RHS 13 D later in the growing season. Both the leaf surfaces are moderately glaucous early in the season, but shinier near mid-summer.

Abaxial margin surface is RHS 137 B on early young leaves, and RHS 137 A on leaves later in the season. The abaxial center color starts RHS 154 D and lightens to RHS 4 D with light and heat as the season progresses. There are also three or more intermediate color patterns between the center and the margin. The most prominent color band is yellow-green RHS 144 B on newly emerged leaves, and between RHS 143 B and RHS 143 C on older leaves. Other more yellow, lighter, or more grayed bands are also sometimes present in thinner and shorter stripes. The main intermediate band visible on the abaxial side is RHS 144 C on young leaves and about RHS 145 C on leaves later in the season. The thinner and shorter bands on the abaxial side are comparable, but slightly lighter than those on the adaxial surface. Petioles are 18 to 22 cm long and 6 to 9 mm wide. The center color starts the same as the leaf center and lightens to RHS 11 D, but varies like the leaves depending on how much light the petiole receives. The edge of the petiole is green RHS 136 A on both surfaces.

*Margin width.*—The leaf blade margin is entire and the green variegation pattern on the edge varies in different regions of the leaf from 10 to 25 mm wide; variable in location on leave and also with age of plant; in young immature plants margins are thinner; increases as plants mature up to about seven to nine years-old.

Flower description:

*Buds.*—Two days prior to opening the buds are violet RHS 85 D and RHS 85 A, 6 to 7 cm long, up to 1.5 cm wide.

*Flowers.*—15 to 21 per scape, funnelform, 4 to 6 cm wide and 6 to 8 cm long, (distal flowers being smaller); no detectable fragrance, persists for a normal period, up to two days, and the scapes remain effective from mid July to late August.

*Tepals.*—arranged in two layers of three, fused at base; with slightly-recurved acute apex; approximately 7 cm long and 1.2 cm wide, the inner three with clear 1 and 2 mm margin, base color in center of tepals Red purple RHS 69D and violet stripes of RHS 84 B. The base of the tepals is between RHS 75 B and 76 B.

*Bract.*—Subtending flowers, 2 cm long and 5 to 7 mm wide with the same colors and pattern as the leaves.

*Peduncle.*—Erect to 48 cm tall and 0.8 cm in diameter, cream color RHS 11 D with tints of green closer to the base, and a reddish purple stippling RHS 60 B becoming much thicker at the apical one fifth.

*Pedicel.*—Approximately 1 cm long, 3 mm wide, between RHS 76 C and RHS D.

*Gynoecium.*—Style — 5 to 6 cm long, 1 mm diameter, near white, curled upward at distal end; Stigma — white, to 3 mm diameter.

*Androecium.*—Filaments — six, white, approximately 1 mm in diameter and to 5 cm long.

*Anthers.*—5 to 6 mm long, 1.5 mm wide, about RHS 83 A around margin of abaxial side, white in center, pollen is yellow-orange RHS 17 B.

Seeds have not been observed.

Disease resistance: The plant is more resistant to melting-out, a condition where the lighter leaf center becomes necrotic, than most other light-centered *Hosta* cultivars. It grows best with plenty of moisture but is able to tolerate some drought. Hardiness to at least USDA zone 3, and other disease resistance is typical of other *Hostas*.

I claim:

1. A new and distinct cultivar of ornamental *Hosta* plant named 'Dancing in the Rain' having light lavender flowers and white-centered leaves with deep green margins, as herein described and illustrated, suitable as a potted plant, for landscaping specimen or in mass, and for fresh-cut arrangements.

* * * * *